United States Patent
Corrigan, Jr.

(10) Patent No.: US 9,463,026 B2
(45) Date of Patent: Oct. 11, 2016

(54) RADIAL COMPRESSION HEMOSTASIS BAND WITH DOPPLER CONFIRMING VASCULAR PATENCY

(71) Applicant: Medical Ingenuities, LLC, Wheaton, IL (US)

(72) Inventor: Richard F. Corrigan, Jr., Wheaton, IL (US)

(73) Assignee: Medical Ingenuities, LLC, Wheaton, IL (US)

( * ) Notice: Subject to any disclaimer, the term of this patent is extended or adjusted under 35 U.S.C. 154(b) by 56 days.

(21) Appl. No.: 14/086,778

(22) Filed: Nov. 21, 2013

(65) Prior Publication Data

US 2014/0142615 A1 May 22, 2014

Related U.S. Application Data

(60) Provisional application No. 61/729,248, filed on Nov. 21, 2012.

(51) Int. Cl.
*A61B 17/00* (2006.01)
*A61B 17/132* (2006.01)

(52) U.S. Cl.
CPC .. *A61B 17/1325* (2013.01); *A61B 2017/00106* (2013.01)

(58) Field of Classification Search
CPC ............ A61B 17/132–17/1355; A61B 17/12; A61B 5/02233; A61B 5/002241; A61B 2017/12004; A61F 5/30; A61F 2013/00468; A61F 2013/0028
USPC ................ 606/201–204; 602/53, 75, 78, 79; 600/490; 601/23, 40, 148–151; 2/338, 2/339, 170, 16–21, 160, 162
See application file for complete search history.

(56) References Cited

U.S. PATENT DOCUMENTS 3,620,209 A * 11/1971 Kravitz ........................... 601/79
4,479,494 A 10/1984 McEwen
(Continued)

FOREIGN PATENT DOCUMENTS

AU WO9846144 A1 10/1998
EP 2404549 A1 8/2011
(Continued)

OTHER PUBLICATIONS

Terumo Medical Corporation, TR Band: Radial Compression Device; p. 10 (Copyright dated 2007) at http://www.terumois.com/admisitration/pdfs/collateral%20library/TR%20Band%20Sell%20sheet.pdf.

(Continued)

*Primary Examiner* — Melanie Tyson
*Assistant Examiner* — Erich Herbermann
(74) *Attorney, Agent, or Firm* — Hovey Williams LLP

(57) ABSTRACT

A hemostatic compression system facilitates patent hemostasis of an arterial access site on the arm of a wearer. The system includes a radial compression band and a Doppler probe. The radial compression band includes an elongated arm band sized to receive the arm. The compression band also includes a pressure surface coupled to the arm band and facing radially inward for compressive engagement with the access site. The Doppler probe is coupled to the arm band adjacent the pressure surface and is configured to sense blood flow through the artery. Hemostatic compression applied by the radial compression band is variable in response to the sensed blood flow so as to ensure patency of the artery during hemostasis of the site.

30 Claims, 3 Drawing Sheets

(56) References Cited

U.S. PATENT DOCUMENTS

| | | | |
|---|---|---|---|
| 4,509,528 A | | 4/1985 | Sahota |
| 4,548,198 A | | 10/1985 | Manes |
| 4,834,802 A | * | 5/1989 | Prier .......................... 606/203 |
| 5,269,803 A | * | 12/1993 | Geary et al. .................. 606/201 |
| 5,307,811 A | * | 5/1994 | Sigwart et al. ............... 600/490 |
| 5,584,853 A | | 12/1996 | McEwen et al. |
| 5,709,647 A | * | 1/1998 | Ferber .......................... 601/134 |
| 5,842,996 A | | 12/1998 | Gruenfeld et al. |
| 6,361,496 B1 | | 3/2002 | Zikorus et al. |
| 6,565,592 B2 | | 5/2003 | Mach |
| 7,331,977 B2 | | 2/2008 | McEwen et al. |
| 7,479,154 B2 | | 1/2009 | McEwen et al. |
| 7,485,131 B2 | | 2/2009 | Hovanes et al. |
| 7,510,530 B2 | | 3/2009 | Hashimoto et al. |
| 8,048,105 B2 | | 11/2011 | McEwen et al. |
| 8,114,026 B2 | | 2/2012 | Leschinsky |
| 8,137,276 B2 | | 3/2012 | Petruzzello et al. |
| 8,231,558 B2 | | 7/2012 | Singh |
| 8,353,834 B2 | | 1/2013 | Routh et al. |
| 8,366,740 B2 | | 2/2013 | McEwen et al. |
| 8,425,426 B2 | | 4/2013 | McEwen et al. |
| 8,721,678 B2 | | 5/2014 | McEwen et al. |
| 8,764,789 B2 | | 7/2014 | Ganske et al. |
| 2006/0122513 A1 | * | 6/2006 | Taylor .......................... 600/459 |
| 2007/0066897 A1 | | 3/2007 | Sekins et al. |
| 2009/0281565 A1 | | 11/2009 | McNeese |
| 2010/0010404 A1 | | 1/2010 | Nardi et al. |
| 2010/0179586 A1 | | 7/2010 | Ward et al. |
| 2011/0028934 A1 | * | 2/2011 | Buckman et al. ....... 604/385.12 |
| 2012/0053617 A1 | | 3/2012 | Benz et al. |
| 2012/0232579 A1 | * | 9/2012 | Lee .............................. 606/202 |
| 2013/0085524 A1 | | 4/2013 | Dahlberg et al. |
| 2013/0190806 A1 | | 7/2013 | McEwen et al. |
| 2013/0237866 A1 | | 9/2013 | Cohen et al. |
| 2014/0012120 A1 | | 1/2014 | Cohen et al. |
| 2014/0024986 A1 | | 1/2014 | Souma |
| 2014/0073973 A1 | | 3/2014 | Sexton et al. |
| 2014/0336697 A1 | | 11/2014 | Masaki |
| 2014/0343600 A1 | | 11/2014 | Leschinsky |

FOREIGN PATENT DOCUMENTS

| | | |
|---|---|---|
| EP | 2708215 A1 | 8/2012 |
| WO | 2009012473 A2 | 1/2009 |
| WO | WO2014027347 A1 | 2/2014 |
| WO | WO2014075627 A1 | 5/2014 |
| WO | WO2014125637 A1 | 8/2014 |

OTHER PUBLICATIONS

Advanced Vascular Dynamics; A leader in post-catheterization hemostasis; (Copyright dated 2013) at www.comporessar.com/products/radial-hemostasis.php.

PCT Search Report and Written Opinion dated Feb. 27, 2014 for PCT/US2013/071320, filed Nov. 21, 2013.

Vascular Solutions, Inc.; 2013 Product Catalog; (Copyright dated 2013) at http://vasc.com/wp-contest/uploads/2011/12/VSI-Product-Catalog-ML-1591-Rev-N.pdf.

NPL from Dec. 31, 2014 letter: Duncan Graham-Rowe, An Ultrasonic Tourniquest to Stop Battlefield Bleeding, MIT Technology at http://www.technology.com/news406163/anultrasonic-tourniquet-to-stop-battlefield-bleeding/.

* cited by examiner

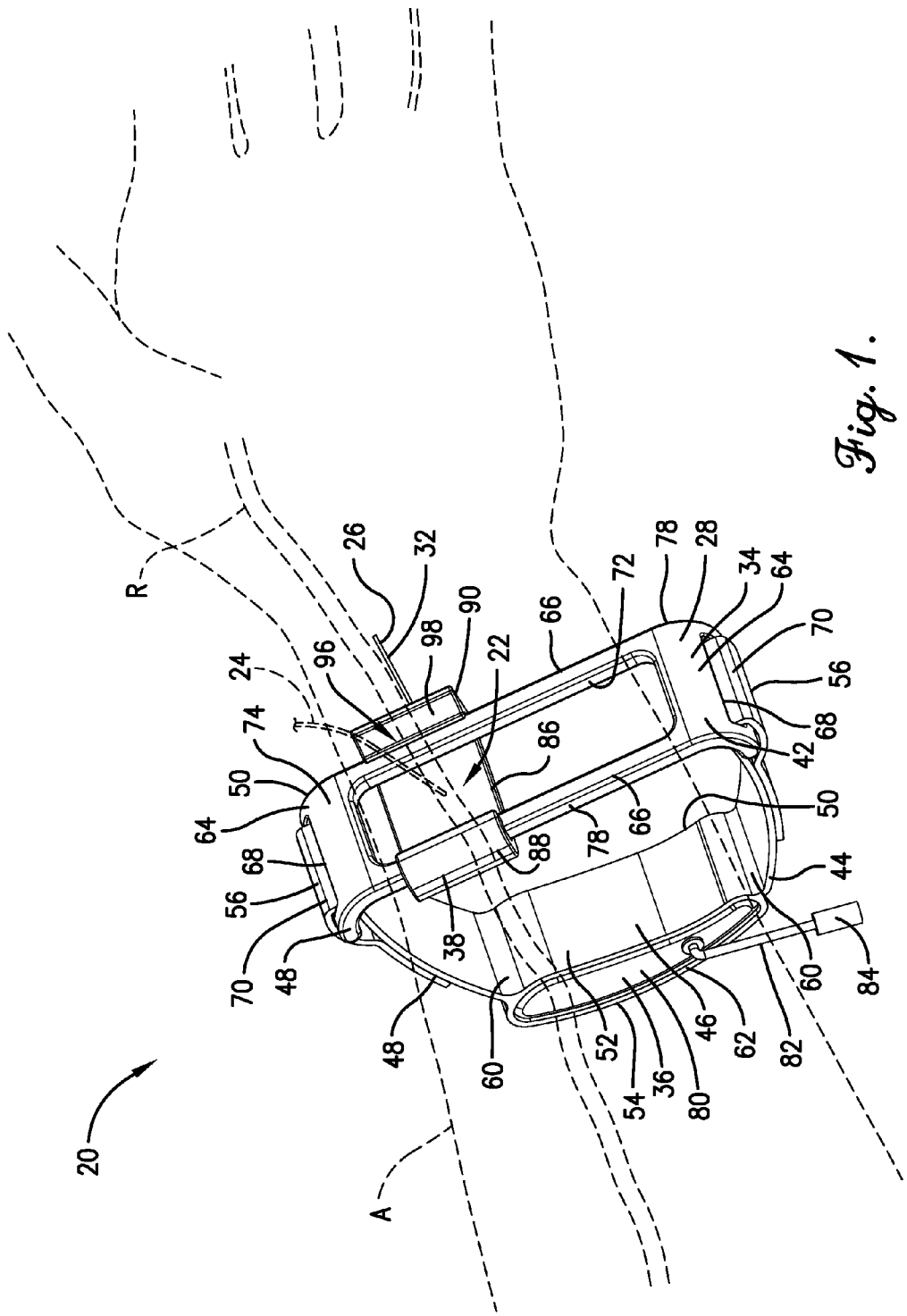

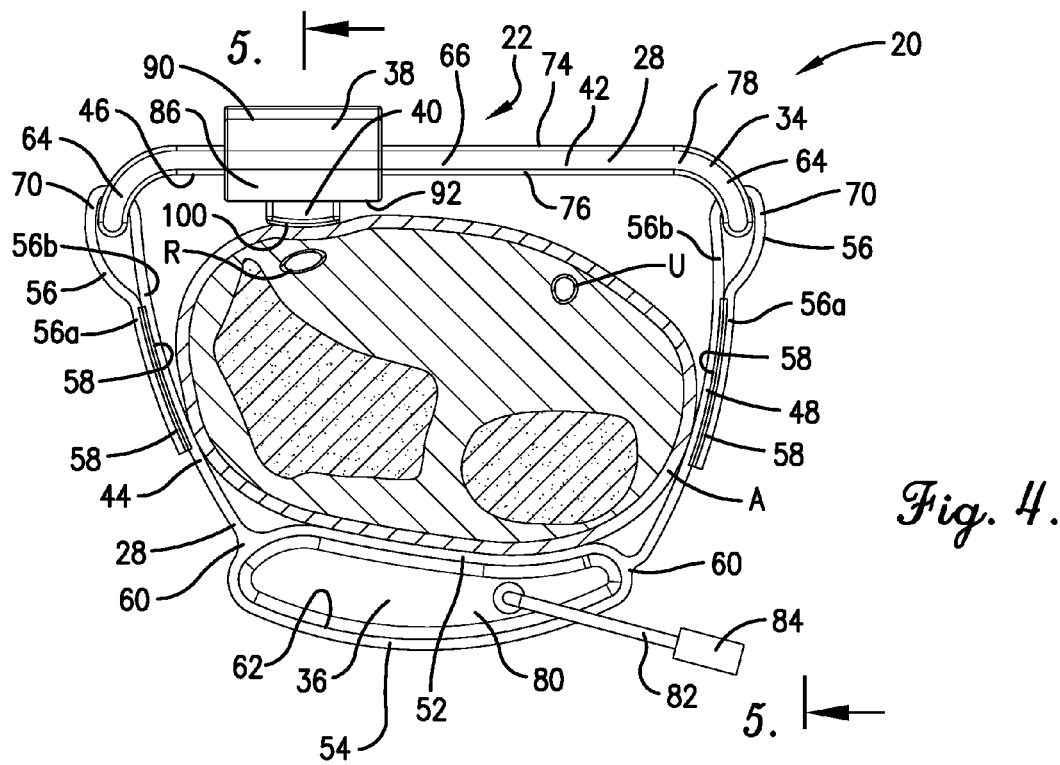
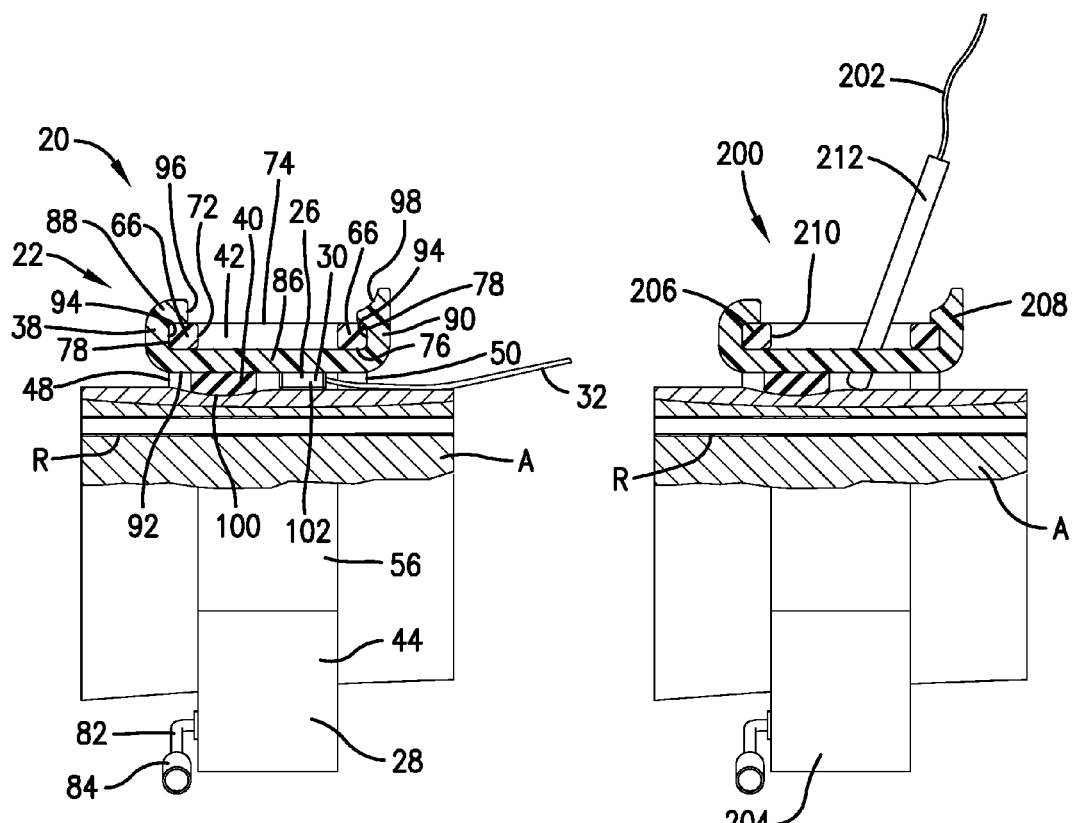

RADIAL COMPRESSION HEMOSTASIS BAND WITH DOPPLER CONFIRMING VASCULAR PATENCY

RELATED APPLICATION

This application claims the benefit of U.S. Provisional Application Ser. No. 61/729,248, filed Nov. 21, 2012, entitled RADIAL COMPRESSION HEMOSTASIS BAND WITH DOPPLER CONFIRMING VASCULAR PATENCY, which is hereby incorporated in its entirety by reference herein.

BACKGROUND

1. Field

The present invention relates generally to hemostat devices. More specifically, embodiments of the present invention concern a hemostatic compression system to gain hemostasis of an arterial access site while maintaining patency of the accessed artery.

2. Discussion of Prior Art

Vascular intervention procedures have long been performed by accessing the femoral artery. However, access of the radial artery has become accepted as an alternative to femoral artery intervention. For instance, it has been found that intervention of the radial artery reduces costs and potential complications when compared to femoral artery invention. Following the intervention, hemostasis of the access site is achieved by applying a hemostasis compression band to the site or by applying manual pressure to the site.

However, certain deficiencies exist with respect to conventional devices for gaining hemostasis of an arterial access site, including those used to provide hemostasis of a radial access site. For instance, conventional hemostasis devices (including compression bands), while being able to provide the necessary pressure to achieve hemostasis, are known to collapse the radial artery when applying pressure. It is also known that the radial artery can be occluded if the artery is either partly or completely collapsed. Occlusion of the radial artery can restrict adequate blood supply to the hand, causing complications such as pain and numbness in the hand.

SUMMARY

The following brief summary is provided to indicate the nature of the subject matter disclosed herein. While certain aspects of the present invention are described below, the summary is not intended to limit the scope of the present invention.

Embodiments of the present invention provide a hemostatic compression system that does not suffer from the problems and limitations of the prior art hemostat devices set forth above.

A first aspect of the present invention concerns a radial compression band configured to provide hemostatic compression to an arterial access site on the arm of a wearer. The radial compression band broadly includes an elongated arm band, an opening-adjustment component, and a pressure pad. The elongated arm band presents an opening sized to receive the arm. The opening-adjustment component is operable to adjust the size of the opening. The pressure pad projects radially inward relative to the arm band for engagement with the access site, with adjustment of the opening size by the component serving to vary the pressure applied by the pad against the access site. The pressure pad is shiftably coupled to the arm band for variable positioning along the length thereof.

A second aspect of the present invention concerns a hemostatic compression system for facilitating patent hemostasis of an arterial access site on the arm of a wearer. The hemostatic compression system broadly includes a radial compression band and a Doppler probe. The radial compression band is configured to provide variable hemostatic compression to the arterial access site. The radial compression band includes an elongated arm band and a pressure surface. The arm band presents an opening sized to receive the arm. The pressure surface is coupled to the arm band to face radially inward for compressive engagement with the access site. The Doppler probe is coupled to the arm band so as to be located adjacent the pressure surface. The Doppler probe is configured to sense blood flow through the artery, with hemostatic compression applied by the radial compression band being variable in response to the sensed blood flow so as to ensure patency of the artery during hemostasis of the site.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Preferred embodiments of the invention are described in detail below with reference to the attached drawing figures, wherein:

FIG. 1 is an upper perspective of a hemostatic compression system constructed in accordance with a preferred embodiment of the present invention, showing a radial compression band and a Doppler probe positioned over a radial access site on a patient's forearm, with the illustrated compression band including arm band, an inflatable bladder, a slider, and a pressure pad;

FIG. 4 is a side elevation of the hemostatic compression system shown in FIGS. 1-3, showing the pressure pad in compressive engagement with the radial access site;

FIG. 5 is a cross section of the hemostatic compression system taken along line 5-5 in FIG. 4; and FIG. 6 is a cross section of an alternative hemostatic compression system similar to FIG. 5, but showing an alternative Doppler probe removably positioned within an access opening of the arm band and coupled relative to the slider.

Figure 3:
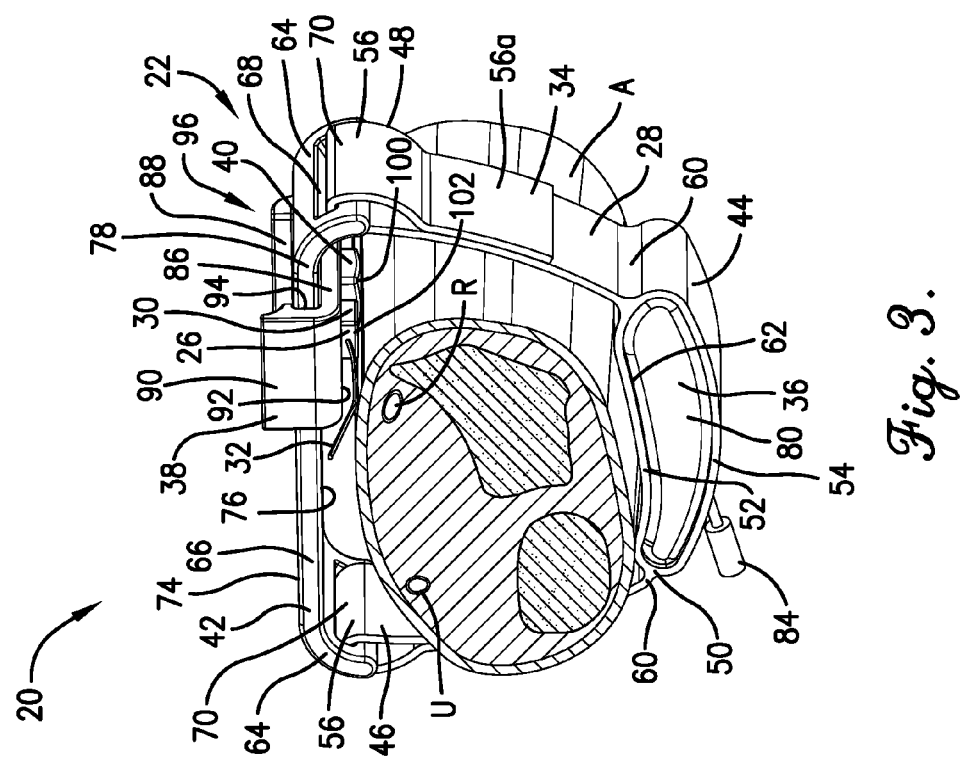
FIG. 3 is a perspective of the hemostatic compression system shown in FIGS. 1 and 2, showing the arm band secured to the forearm and the pressure pad in compressive engagement with the radial access site.
Figure 2:
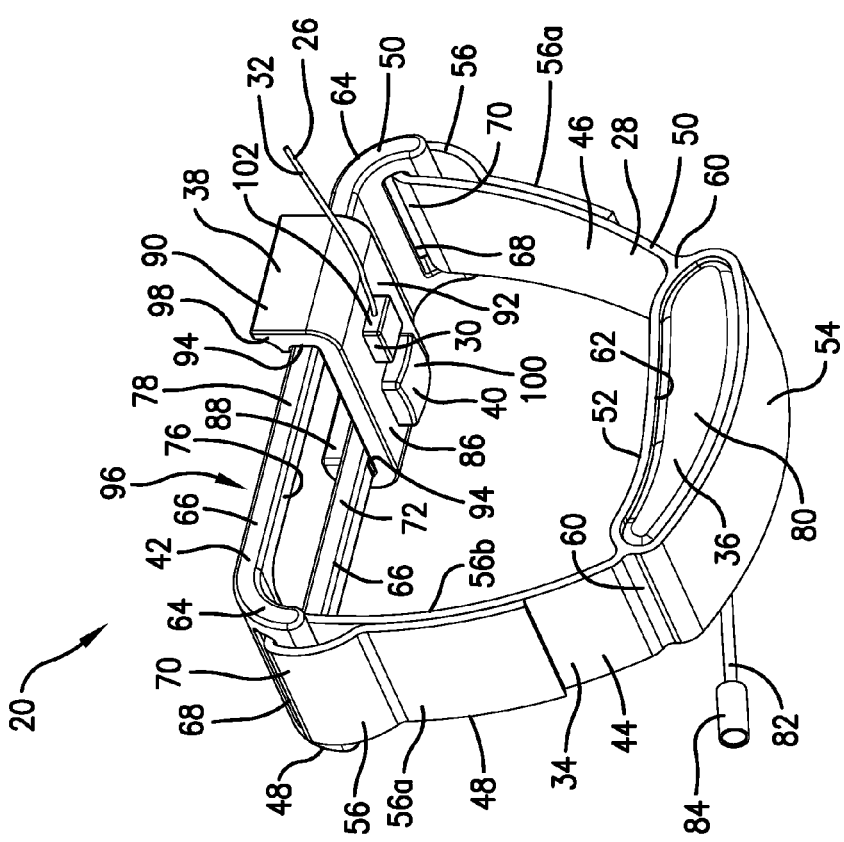
FIG. 2 is a lower perspective of the hemostatic compression system shown in FIG. 1, showing a pressure pad and the Doppler probe mounted on a lower surface of the slider, with the pressure pad being diametrically opposed to the bladder.

The drawing figures do not limit the present invention to the specific embodiments disclosed and described herein.

The drawings are not necessarily to scale, emphasis instead being placed upon clearly illustrating the principles of the preferred embodiment.

DETAILED DESCRIPTION OF THE PREFERRED EMBODIMENTS

Turning initially to FIG. 1, a radial hemostatic compression system 20 is constructed in accordance with a preferred embodiment of the present invention. The system 20 is preferably used to selectively gain hemostasis of an arterial access site 22 along a patient's forearm A and to confirm vascular patency while achieving hemostasis. That is, the illustrated system 20 is preferably configured to establish patent hemostasis of the access site 22 so as to maintain blood flow through the artery.

The illustrated section of the forearm A includes a distally extending radial artery R and a distally extending ulnar artery U (see FIGS. 3 and 4). A catheter 24 penetrates the illustrated access site 22 to access the radial artery R (see FIG. 1). While the catheter 24 is illustrated as being inserted into the access site 22 while the system 20 is located on the forearm A, the catheter 24 can be removed from the access site 22 either before or after the system 20 is positioned on the forearm A. While the illustrated system 20 is preferably used in connection with accessing the radial artery R, it is within the ambit of the present invention where the system 20 is used with another artery. The system 20 broadly includes a Doppler ultrasound system 26 and a radial compression band 28.

The Doppler ultrasound system 26 preferably comprises a conventional ultrasound instrument to perform a vascular Doppler ultrasound. In the usual manner, the Doppler ultrasound system 26 preferably includes a Doppler probe 30 with a transducer (not shown) and a Doppler unit (not shown) connected to the probe by a cord 32. The Doppler probe 30 is operable to be located adjacent an artery, such as the radial artery R, to sense blood flow through the artery. The illustrated Doppler probe 30 is preferably attached to the radial compression band 28, as will be discussed.

Turning to FIGS. 1-5, the radial compression band 28 is used to apply radial pressure to the forearm A, particularly along the access site 22. The radial compression band 28 preferably includes an elongated arm band 34, an inflatable bladder 36, a slider 38, and a pressure pad 40.

The elongated arm band 34 preferably provides an elongated strength member that can be maintained under tension while applying compression to the access site 22. The elongated arm band 34 also preferably serves to support the bladder 36 and slider 38. The illustrated arm band 34 preferably includes a frame 42 and an adjustable strap 44 adjustably attached to the frame 42. The arm band 34 also presents an arm opening 46 that extends between proximal and distal margins 48,50 to receive the forearm A.

The adjustable strap 44 is elongated and preferably includes interior and exterior central sections 52,54 and opposite end sections 56 that are preferably formed of a flexible strap material. The flexible strap material preferably includes a synthetic resin and, more preferably, includes a synthetic resin fabric material. However, the strap 44 could include other materials without departing from the scope of the present invention.

The adjustable strap 44 also preferably includes hook-and-loop material attached along the end sections. In particular, each end section 56 has a pair of folds 56a,b that receive respective hook material and loop material strips 58 (see FIG. 4). Thus, the folds 56a,b can be positioned in secure engagement with one another. In this manner, the end sections 56 of the strap 44 are preferably used to secure the adjustable strap 44 to the frame 42. Furthermore, the end sections 56 also serve to provide adjustability to the overall circumferential length of the arm band 34 such that the arm opening size may be varied by adjusting the end sections 56. However, the strap 44 could be alternatively attached to the frame 42 without departing from the scope of the present invention.

The central sections 52,54 are preferably attached to one another along connected end margins 60 and cooperatively form a bladder opening 62 to receive and secure the bladder 36 to the adjustable strap 44. The bladder 36 is preferably attached to the strap 44 with stitching (not shown), although the bladder 36 could be attached to the strap 44 by other means (such as adhesive). Yet further, the bladder 36 could be completely covered and encapsulated by the strap 44. In the illustrated embodiment, the interior central section 52 is preferably more flexible and elastic than the exterior central section 54. In other words, the interior central section 52 preferably elongates to a greater degree than the exterior central section 54 in response to the same force. As a result, when the bladder 36 expands, the interior central section 52 preferably elongates more than the exterior central section 54. More preferably, the interior central section 52 preferably elongates to a much greater degree than the exterior central section 54. In some instances, any elongation of the exterior central section 54 in response to bladder expansion may be imperceptible.

The illustrated frame 42 preferably comprises a rigid and unitary structure. The frame 42 preferably includes curved connector ends 64 and frame rails 66 that interconnect the connector ends 64. The connector ends 64 each present a slot 68 to receive a corresponding one of the end sections 56 of the strap 44. Thus, each end section 56 can be fed through a respective slot 68 and folded onto itself to secure the end section 56 to the respective connector end 64 and thereby provide a removable connection 70 between the frame 42 and strap 44. As previously noted, this removable connection 70 also allows each end section 56 to be adjustably connected to the frame 42 (e.g., to change the size of the arm opening 46).

Notably, the adjustable connections 70 between the frame 42 and strap 44 preferably permit the arm band 34 to be quickly and conveniently applied to (and removed from) the forearm A. The adjustable connections 70 also preferably allow for quick and reliable adjustment of the arm opening 46 (and thereby provide adjustment of the fit of the arm band 34 relative to the forearm A). Thus, for instance, the connections 70 can be loosened in the event that the arm band 34 is too snugly secured onto the forearm A. That is, the connections 70 can be adjusted to vary compression applied by the radial compression band 28. While perhaps not comprising a most preferred process to achieve hemostasis, the connections 70 could be used to adjust the pressure applied to the access site 22 by the pressure pad 40 to produce hemostasis. In any event, the illustrated connections 70 are convenient and efficient for securing and removing the arm band 34. However, the principles of the present invention are applicable where alternative connection components (such as other types of adjustable connections) are provided between the frame 42 and strap 44 to permit selective attachment and removal of the arm band 34. Similarly, it is also within the ambit of the present invention where alternative connection components are provided between the frame 42 and strap 44 to adjustably size the arm opening 46. Yet further, the principles of the present invention are also applicable to elimination of the adjustable connection components altogether. In such an alternative, the arm band 34 can be provided as an elastic strap stretched onto the patent's forearm or in multiple sizes with the appropriate band being selected based on the patient's forearm size.

The illustrated frame rails 66 are preferably spaced apart from one another to define an access opening 72 therebetween (see FIG. 1). As will be discussed, the access opening 72 is configured to expose and permit access to the access site 22 when the band 28 is secured on the forearm A.

Again, the illustrated frame 42 is preferably rigid (relative to the strap 44), but it is within the ambit of the present invention where at least part of the frame 42 has some flexibility (e.g., where the frame 42 can bend around the forearm A). The frame 42 may also be preshaped to curve around the forearm A. The frame 42 preferably includes a hard synthetic resin material to provide the desired rigidity and resiliency. However, the frame 42 could include other materials without departing from the scope of the present invention. Yet further, the frame 42 is preferably made of a material that is substantially transparent (e.g., so that the access site 22 can be clearly viewed while the frame 42 extends over the access site 22).

The frame 42 preferably presents upper and lower surfaces 74,76 and outer side surfaces 78, with the side surfaces 78 preferably extending parallel to one another and forming part of the proximal and distal margins 48,50. The illustrated access opening 72 is preferably spaced between the side surfaces 78. In this manner, the frame 42 provides a suitably strong and resilient band structure while providing visual and physical access to the access site.

It is within the scope of the present invention where the frame 42 is alternatively shaped and/or configured. For instance, the rails 66 could be alternatively shaped or configured. Also, the access opening 72 could be alternatively sized and configured without departing from the scope of the present invention.

Although the arm band 34 preferably includes a single adjustable strap 44, the principles of the present invention are applicable where the arm band 34 includes a pair of straps that cooperate with the frame 42 to secure the arm band 34 on the forearm A. For instance, the pair of alternative straps could be attached to respective connector ends 64 of the frame 42 and adjustably attached to one another.

While the illustrated arm band 34 preferably extends continuously about and fully encircles the arm opening 46, it is also within the ambit of the present invention where the arm band 34 is not continuous. For instance, the arm band 34 could include a pair of resilient band sections attached to corresponding connector ends 64 of the frame 42 but not to one another. In such an alternative embodiment, the resilient band sections could cooperate with the frame 42 to resiliently provide the arm opening 46, with the band sections each having ends that are not directly attached to one another or to the frame 42, but are located at or adjacent to one another. Furthermore, such band sections could flex to allow separation of the unattached band section ends to permit the alternative arm band to be positioned on the arm or removed therefrom.

The illustrated bladder 36 is preferably used to selectively adjust the size the arm opening 46. The bladder 36 preferably includes a wall 80 that encloses a chamber (not shown), a tube 82 that fluidly communicates with the chamber, and a valve 84 operable to be connected to a syringe (not shown). The bladder 36 is operable to receive fluid (preferably air) from the syringe and to thereby be expanded.

The illustrated bladder 36 is preferably secured between the interior and exterior sections 52,54. Because the interior section 52 is more flexible and elastic than the exterior section, expansion of the bladder 36 causes more elongation (and deflection) of the interior section 52 than the exterior section 54. Thus, the bladder and strap 44 cooperate so that bladder expansion preferably reduces the size of the arm opening 46. Conversely, bladder contraction preferably enlarges the size of the arm opening 46.

Once the band 28 is secured on the forearm A by adjusting and securing the end sections 56, adjustment of compression applied to the access site 22 is preferably provided by adjusting the bladder 36. It has been found that pressure adjustment of the bladder provides precise and efficient adjustment of compression applied to the access site 22. While the bladder is preferably provided to adjust the arm opening size, an alternative adjustment component could be provided to adjust the size of the arm opening 46 to control compression applied to the access site 22. For example, the sections 52,54 could be configured to receive one or more variously sized inserts that provide variable pressure based on the size of the patient's forearm and the insert(s) selected.

The illustrated slider 38 is used to selectively position the Doppler probe 30 and pressure pad 40 relative to the access site 22. The slider 38 preferably comprises an elongated unitary mounting structure and includes a body 86 and opposite wrap-around tabs 88,90 that serve as connectors. The body 86 presents a lower surface 92. Each tab 88,90 presents an open channel 94 that is operable to slidably receive a corresponding one of the rails 66 (see FIGS. 2 and 5). The tabs 88,90 cooperatively define an opening 96 through which the frame 42 can be passed (i.e., to attach and detach the slider 38 and the frame 42). While the slider 38 is preferably slidably mounted on the frame 42 to be selectively positioned along the length of the arm band 34, it is also within the ambit of the present invention where the slider 38 is alternatively adjusted between multiple locations along the arm band 34.

The slider 38 preferably includes a synthetic resin material, although the slider 38 could include other materials without departing from the scope of the present invention. Also, the slider 38 is preferably made of a material that is substantially transparent (e.g., so that the access site 22 can be clearly viewed while the slider 38 is positioned over the access site 22). The illustrated slider 38 is preferably resiliently flexible to flex into and out of sliding engagement with the frame 42.

The tab 90 also preferably presents a contoured gripping ledge 98. The ledge 98 is operable to be grasped or otherwise engaged by a user to flex the slider 38 so that the tabs 88,90 are moved away from one another (i.e., to enlarge the opening 96). Thus, because the slider 38 is preferably designed to permit such resilient flexing, the opening 96 can be expanded to selectively mount the slider 38 on and remove the slider 38 from the frame 42.

The illustrated slider 38 is preferably configured to slide along the length of the frame 42 and between the connector ends 64. However, it is also within the scope of the present invention where the slider 38 can move or otherwise be positioned along locations of the arm band 34 other than the frame 42. Furthermore, variable positioning of the pressure pad 40 and Doppler probe 30 can be accomplished without the slider altogether. For example, the pad 40 and probe 30 could be fixed to a component that is connectable to the arm band 34 at multiple locations (e.g., discrete snaps, hook-and-loop fastening strips, etc.).

The pressure pad 40 is configured to apply pressure to and achieve hemostasis of the access site 22. The pressure pad 40 preferably comprises a unitary body and presents a generally convex pressure surface 100. The illustrated pressure surface 100 faces radially inwardly relative to the arm band 34 for compressive engagement with the access site 22. The pressure pad 40 is preferably fixed to the lower surface 92 of the slider 38 so that the pressure pad 40 and slider 38 move with one another along the length of the frame 42. However, it will be appreciated that the pressure pad 40 could be alternatively shaped and/or configured to provide the pressure surface 100 without departing from the scope of the present invention. For instance, the pressure pad 40 could be enlarged to present a larger pressure surface 100 and thereby increase the surface area for engaging the access site 22. Yet further, the principles of the present invention are applicable where the pressure surface 100 is provided by a component other than the pressure pad 40 (e.g., where the pressure surface 100 is provided by the frame 42).

The illustrated pressure pad 40 is preferably diametrically opposed to the bladder 36. In this manner, compressive force applied by the pressure pad 40 to the access site 22 is produced at least partly by compressive force applied by the bladder 36. Furthermore, this preferred arrangement between the bladder 36 and the pressure pad 40 permits the force applied by the pressure pad 40 to be readily controlled by adjusting inflation of the bladder 36. Specifically, the force applied by the pressure pad 40 can be increased by inflating the bladder 36. Conversely, the force applied by the pressure pad 40 can be reduced by deflating the bladder 36 (assuming the bladder 36 is inflated).

Again, it is within the ambit of the present invention where the catheter 24 is removed from the access site 22 either before or after the system 20 is positioned on the forearm A. Also, the bladder 36 can be inflated or deflated (e.g., to bring the pressure pad 40 into engagement with the access site 22) either prior to or after removal of the catheter 24. For instance, subsequent to catheter removal, the bladder 36 can be inflated by the syringe to achieve hemostasis of the access site 22. Generally, the bladder 36 is gradually inflated while visually checking the access site 22 to confirm that blood flow out of the access site 22 has ceased. Again, because the frame 42 and slider 38 are both substantially transparent, the access site 22 can be clearly viewed even as the slider 38 and frame 42 are positioned over the access site 22. Once hemostasis of the access site 22 is gained, further inflation of the bladder 36 can be stopped. Furthermore, in some instances, after hemostasis is achieved, the bladder 36 could be deflated without losing hemostasis of the access site 22.

The Doppler probe 30 preferably includes a transducer (not shown) mounted within a housing 102, as well as the cord 32 connected to the housing 102. The Doppler probe 30 is preferably fixed to the lower surface 92 of the slider 38 adjacent to the pressure pad 40. More preferably, the Doppler probe 30 is preferably located distally of the pressure pad 40. Thus, when the slider is located to position the pressure pad 40 over the access site 22, the Doppler probe 30 is positioned adjacent the access site 22 to sense any distal blood flow through the radial artery R past the access site 22. In this manner, the Doppler probe 30 is positioned to confirm patency of the radial artery R adjacent the access site 22 while achieving hemostasis of the access site 22. Furthermore, mounting of the Doppler probe 30 to the slider 38 preferably permits the Doppler ultrasound system 26 to be supported for extended monitoring of arterial blood flow (e.g., where arterial blood flow is monitored by the Doppler probe 30 for 2-3 hours).

While the pressure pad 40 is compressing the access site 22 to gain hemostasis, the Doppler system 26, including the Doppler probe 30, is preferably used to confirm a distal flow of blood through the radial artery R. If the Doppler system 26 senses that the distal blood flow through the artery R is diminished from a normal flow rate or is stopped entirely, the bladder 36 can be gradually deflated to reduce the compressive pressure applied to the access site 22. Once patency of the artery R is confirmed, deflation of the bladder 36 may be ceased to maintain pressure on the access site 22 and thereby maintain hemostasis of the access site 22. However, in some instances, pressure on the access site 22 could be slightly increased or decreased to maintain hemostasis while ensuring patency of the artery R.

In use, the system 20 is initially attached to the forearm A while the access site 22 is being accessed by catheter 24. Specifically, the radial compression band 28 is located on the forearm A by positioning the frame 42 and slider 38 along the underneath side of the forearm A while wrapping the strap 44 around the upper side of the forearm A. The end sections 56 of the strap 44 are secured to corresponding connector ends 64 so that the radial compression band 28 is snugly secured to the forearm A. The slider 38 is also positioned so that the pressure pad 40 is positioned over the access site 22. If necessary, the slider 38 can be moved along the length of the frame 42 to properly position the pressure pad 40.

Again, the system 20 can be positioned on the forearm A either before or after the catheter 24 is removed from the access site 22. Once the catheter 24 is removed, the bladder 36 may be inflated or deflated. For instance, the bladder 36 can be inflated by the syringe to achieve hemostasis of the access site 22. Generally, the bladder 36 is gradually inflated while visually checking the access site 22 to confirm that blood flow out of the access site 22 has ceased. Once hemostasis of the access site 22 is gained, further inflation of the bladder 36 can be stopped.

While the bladder 36 is being inflated (or is inflated) to gain hemostasis, the Doppler system 26, including the Doppler probe 30, is preferably used to confirm a distal flow of blood through the radial artery R. If the Doppler system 26 senses that the distal blood flow through the artery R is diminished from a normal flow rate or is stopped entirely, the bladder 36 can be gradually deflated to reduce the compressive pressure applied to the access site 22. Once patency of the artery R is confirmed, deflation of the bladder 36 may be ceased to maintain pressure on the access site 22 and thereby maintain hemostasis of the access site 22. Again, in some instances, pressure on the access site 22 could be slightly increased or decreased to maintain hemostasis while ensuring patency of the artery R.

Turning to FIG. 6, an alternative hemostatic compression system 200 is disclosed. For the sake of brevity, the remaining description will focus primarily on the differences of this alternative embodiment compared to the embodiment described above. The alternative system 200 broadly includes an alternative Doppler ultrasound system 202 and a radial compression band 204. The radial compression band 204 includes a frame 206 and a slider 208, with the frame 206 presenting an access opening 210.

The Doppler ultrasound system 202 includes an alternative Doppler probe 212. The Doppler probe 212 is preferably removably coupled to one side of the slider 208 and is positioned within and projects through the access opening 210. However, it is within the ambit of the present invention where the Doppler probe 212 is not coupled to the radial compression band 204.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and assess the reasonably fair scope of the present invention as pertains to any apparatus not materially departing from but outside the literal scope of the invention as set forth in the following claims.

What is claimed is:

1. A radial compression band configured to provide hemostatic compression to an arterial access site on the arm of a wearer, said radial compression band comprising:
    an elongated arm band presenting an arm opening sized to receive the arm;
    said arm band presenting proximal and distal margins, with the arm opening being defined between the margins,
    an opening-adjustment component operable to adjust the size of the arm opening; and
    an arterial pressure pad projecting radially inward relative to the arm band for engagement with the access site, with adjustment of the arm opening size by the component serving to vary the pressure applied by the pad against the access site,
    said arm band presenting a window located between the proximal and distal margins so as to expose the underlying portion of the arm,
    said pressure pad located radially inboard of the window and extending across at least part of the window so as to visibly facilitate engagement of the pressure pad with the access site.

2. The radial compression band as claimed in claim 1, said arm band having an adjustable length so that the arm opening size is adjustably defined by the arm band and further adjustable by the opening-adjustment component.

3. The radial compression band as claimed in claim 2, said arm band including at least one adjustment strap that permits selective adjustment of the length of the arm band.

4. The radial compression band as claimed in claim 3, said arm band being continuous so as to fully encircle the arm opening.

5. The radial compression band as claimed in claim 1, said opening-adjustment component and the pressure pad being generally diametrically opposed from one another.

6. The radial compression band as claimed in claim 1, said arm band including an elongated frame extending lengthwise along the band,
    said pressure pad being shiftable along the length of the frame.

7. The radial compression band as claimed in claim 6, said arm band including a slider connected to the frame for sliding movement along the length thereof,
    said pressure pad being fixed to the slider.

8. The radial compression band as claimed in claim 6, said opening-adjustment component and the pressure pad being generally diametrically opposed from one another.

9. The radial compression band as claimed in claim 6, said frame presenting the window located between the proximal and distal margins.

10. The radial compression band as claimed in claim 6, said frame presenting opposite frame ends,
    said arm band including a flexible strap interconnecting the frame ends,
    said frame being at least substantially rigid relative to the strap.

11. The radial compression band as claimed in claim 1, said opening-adjustment component including an expandable bladder positioned in generally diametric opposition to the pressure pad.

12. The radial compression band as claimed in claim 11, said arm band including an elongated frame extending lengthwise along the band to present opposite frame ends,
    said pressure pad being shiftable along the length of the frame,
    said arm band including a flexible strap interconnecting the frame ends,
    said expandable bladder being coupled to the flexible strap.

13. The radial compression band as claimed in claim 1, further comprising:
    a pressure-applying body that includes the pressure pad, with at least part of the body being transparent to permit viewing of the access site when the body is positioned over the access site.

14. The radial compression band as claimed in claim 13, said arm band including an elongated frame and the pressure-applying body,
    said frame extending lengthwise along the band and presenting the window,
    said body including a slider connected to the frame for sliding movement along the length thereof, with the slider being transparent,
    said pressure pad being fixed to the slider.

15. A hemostatic compression system for facilitating patent hemostasis of an arterial access site on the arm of a wearer, said hemostatic compression system comprising:
    a radial compression band configured to provide variable hemostatic compression to the arterial access site, said radial compression band including
        an elongated arm band presenting an arm opening sized to receive the arm, and
        an arterial pressure surface coupled to the arm band to face radially inward for compressive engagement with the access site,
        said arm band presenting proximal and distal margins, with the arm opening being defined between the margins,
        said arm band presenting a window located between the proximal and distal margins so as to expose the underlying portion of the arm,
        said pressure surface located radially inboard of the window and extending across at least part of the window so as to visibly facilitate engagement of the pressure surface with the access site; and
    a Doppler probe coupled to the arm band so as to be located adjacent the pressure surface,
        said Doppler probe being configured to sense blood flow through the artery, with hemostatic compression applied by the radial compression band being variable in response to the sensed blood flow so as to ensure patency of the artery during hemostasis of the site.

16. The hemostatic compression system as claimed in claim 15,
    said arm band having an adjustable length so that the arm opening size is adjustably defined by the arm band, with adjustment of the arm opening size serving to vary the pressure applied by the pressure surface.

17. The hemostatic compression system as claimed in claim 16,
    said arm band including at least one adjustment strap that permits selective adjustment of the length of the arm band.

18. The hemostatic compression system as claimed in claim 17,
    said arm band being continuous so as to fully encircle the arm opening.

19. The hemostatic compression system as claimed in claim 15,
    said radial compression band including an opening-adjustment component operable to further adjust the size of the opening.

20. The hemostatic compression system as claimed in claim 15,
    said radial compression band including an opening-adjustment component operable to adjust the size of the opening,
    said opening-adjustment component and the pressure surface being generally diametrically opposed from one another.

21. The hemostatic compression system as claimed in claim 15,
    said arm band including an elongated frame extending lengthwise along the band,
    said pressure surface being shiftable along the length of the frame.

22. The hemostatic compression system as claimed in claim 21,
    said arm band including a slider connected to the frame for sliding movement along the length thereof,
    said pressure surface being fixed to the slider.

23. The hemostatic compression system as claimed in claim 22,
    said Doppler probe being fixed to the slider.

24. The hemostatic compression system as claimed in claim 21,
    said radial compression band including an opening-adjustment component operable to adjust the size of the opening,
    said opening-adjustment component and the pressure surface being generally diametrically opposed from one another.

25. The hemostatic compression system as claimed in claim 21,
    said frame presenting the window located between the proximal and distal margins.

26. The hemostatic compression system as claimed in claim 25,
    said Doppler probe projecting through the window.

27. The hemostatic compression system as claimed in claim 21,
    said frame presenting opposite frame ends,
    said arm band including a flexible strap interconnecting the frame ends,
    said frame being at least substantially rigid relative to the strap.

28. The hemostatic compression system as claimed in claim 15,
    said radial compression band including an opening-adjustment component operable to adjust the size of the opening,
    said opening-adjustment component including an expandable bladder positioned in generally diametric opposition to the pressure surface.

29. The hemostatic compression system as claimed in claim 28,
    said arm band including an elongated frame extending lengthwise along the band to present opposite frame ends,
    said pressure surface being shiftable along the length of the frame,
    said arm band including a flexible strap interconnecting the frame ends,
    said expandable bladder being coupled to the flexible strap.

30. The hemostatic compression system as claimed in claim 15,
    said radial compression band including a pressure pad projecting radially inward relative to the arm band,
    said pressure pad defining the pressure surface.

* * * * *